United States Patent
Blomqvist

(10) Patent No.: US 8,679,026 B2
(45) Date of Patent: Mar. 25, 2014

(54) MEDICAL DEVICE FOR DETECTING PULMONARY ARTERY PRESSURE

(75) Inventor: Andreas Blomqvist, Spånga (SE)

(73) Assignee: St. Jude Medical, AB, Jarfalla (SE)

( * ) Notice: Subject to any disclaimer, the term of this patent is extended or adjusted under 35 U.S.C. 154(b) by 975 days.

(21) Appl. No.: 12/679,711

(22) PCT Filed: Nov. 8, 2007

(86) PCT No.: PCT/SE2007/000989
§ 371 (c)(1),
(2), (4) Date: Mar. 24, 2010

(87) PCT Pub. No.: WO2009/041867
PCT Pub. Date: Apr. 2, 2009

(65) Prior Publication Data
US 2010/0286535 A1    Nov. 11, 2010

(30) Foreign Application Priority Data

Sep. 24, 2007 (WO) .................. PCT/SE2007/050673

(51) Int. Cl.
*A61B 5/0215*    (2006.01)
*A61B 5/021*     (2006.01)

(52) U.S. Cl.
USPC .............................. 600/486; 600/485; 600/481

(58) Field of Classification Search
USPC ...................... 600/481, 485–488; 607/17–26
See application file for complete search history.

(56) References Cited

U.S. PATENT DOCUMENTS

| | | | |
|---|---|---|---|
| 5,003,976 A * | 4/1991 | Alt ................................. | 607/18 |
| 5,800,467 A * | 9/1998 | Park et al. ...................... | 607/17 |
| 6,368,283 B1 | 4/2002 | Xu et al. | |
| 6,865,419 B2 | 3/2005 | Mulligan et al. | |
| 7,024,244 B2 | 4/2006 | Muhlenberg et al. | |
| 2002/0103442 A1 * | 8/2002 | Mulligan et al. .............. | 600/513 |
| 2003/0199813 A1 | 10/2003 | Struble | |
| 2005/0177062 A1 | 8/2005 | Skrabal et al. | |
| 2006/0116590 A1 | 6/2006 | Fayram et al. | |
| 2006/0167359 A1 * | 7/2006 | Bennett et al. ................ | 600/485 |
| 2006/0167361 A1 | 7/2006 | Bennett et al. | |
| 2006/0167516 A1 * | 7/2006 | Kjellstrom et al. ............ | 607/23 |
| 2007/0060959 A1 | 3/2007 | Salo et al. | |
| 2007/0088221 A1 * | 4/2007 | Stahmann ...................... | 600/485 |
| 2007/0213778 A1 * | 9/2007 | Burnes et al. .................... | 607/9 |
| 2007/0282210 A1 | 12/2007 | Stern | |
| 2008/0288013 A1 * | 11/2008 | Schecter ........................ | 607/23 |
| 2013/0184545 A1 * | 7/2013 | Blomqvist et al. ............ | 600/325 |

OTHER PUBLICATIONS

"Arterial Pulse." Ranganathan et al. The Art and Science of Cardiac Physical Examination. 2006. pp. 15-48.*

(Continued)

*Primary Examiner* — Navin Natnithithadha
*Assistant Examiner* — Meredith Weare

(57) ABSTRACT

In a medical device and method to monitor pulmonary artery pressure of a patient, a first parameter related to the right ventricular straight volume of the patient's is detected, and a second parameter related to the right ventricular ejection rate of the patient's heart, or related to the workload of the patient's heart, is also determined. A pulmonary pressure index is determined by combining the first and second parameters, with variations of the pulmonary pressure index indicating variations in the pulmonary artery pressure. Pulmonary artery hypertension can be monitored with such a device and method.

29 Claims, 3 Drawing Sheets

(56) References Cited

OTHER PUBLICATIONS

"Right Ventricular Function and Failure: Report of a National Heart, Lung, and Blood Institute Working Group on Cellular and Molecular Mechanisms of Right Heart Failure." Voelkel et al. Circulation. 2006;114:1883-1891.*

"Evaluation of Pulmonary Arterial End-Diastolic Pressure as an Estimate of Left Ventricular End-Diastolic Pressure in Patients with Normal and Abnormal Left Ventricular Performance." Bouchard et al. Circulation. 1971;44:1072-1079.*

Ioninvasive Estimates of Pulmonary Hypertension and study of the Etiology of Ejection Flow Velocity Profiles, Sasaki et al, Journal of Cardiography, vol. 15 (1985) pp. 1251-1261.

* cited by examiner

MEDICAL DEVICE FOR DETECTING PULMONARY ARTERY PRESSURE

BACKGROUND OF THE INVENTION

1. Field of the Invention

The present invention relates to a medical device and to a method in a medical device according to the preambles of the independent claims adapted to detect and monitor Pulmonary Artery Pressure (PAP). In particular the invention relates to a medical device and to a method adapted to detect and monitor Pulmonary Artery Hypertension (PAH) or Heart Failure (HF).

2. Description of the Prior Art

Heart failure is the failure of your heart muscle to pump enough blood to meet your body's needs. About 4.8 million people in the United States have heart failure. It is the major cause of admission to the hospital for those over 65 years old. There are many reasons why the heart muscle becomes weak.

When the heart muscle pump cannot handle the amount of blood it gets, the blood slows down and backs up. This puts pressure on the blood vessels in the lungs, legs and abdomen and causes leaking from these blood vessels. Fluid collects in the tissues, which can cause you to have leg swelling, shortness of breath, lack of appetite or abdominal pain. This backup of blood is called heart failure. The heart chambers get bigger over time to decrease the backup. Although this helps in the early stages, it makes the heart pump worse in the long run. Cardiomegaly is the name for when the heart chamber gets bigger.

There are many reasons why the blood backs up. The heart may become stressed and cannot pump as well. The amount of blood (fluid) that the heart has to pump may increase. Heart failure decreases the kidney's ability to remove salt (sodium) and water from your body. Because your kidneys get less blood, they think that the body needs more blood volume. To make up for this, your body puts out a hormone that makes you hold salt and water. This hormone increases as the heart's pumping ability becomes worse. That is why fluid retention becomes worse as the heart becomes weaker.

The pressure in the pulmonary artery is usually much lower than in the aorta. As a natural way to deal with this the left ventricle is much stronger than the right ventricle and can therefore deal with the higher pressures and higher pressure gradients in the left side. However, when pressure increases on the right side, the right ventricle is not equipped to handle the increased demand on myocardial performance. Hypertrophy most likely occurs and this will inevitably lead to right-sided heart failure. Symptoms may then be swollen feet as a result of fluids backing up in the body as the right side of the heart can not manage to pump away the blood returning from the body, due to the high pressure required to open the pulmonary valve, causing the congestion. This is known as peripheral oedema.

Pulmonary artery hypertension (PAH), also referred to as pulmonary hypertension (PHT), is often idiopathic and the patients are also often symptom free for quite some time. These two facts lead to that this disease often goes on unnoticed for quite some time, delaying any potential care. Two types of PAH may be identified: Primary pulmonary arterial hypertension (PPAH) that is inherited or occurs for no known reason and Secondary pulmonary arterial hypertension (SPAN) that either is caused by, or occurs because of, another condition. The condition includes chronic heart or lung disease, blood clots in the lungs, or a disease like scleroderma.

Described more in detail, PAH is continuous high blood pressure in the pulmonary artery and the average blood pressure in a normal pulmonary artery is about 14 mmHg when the person is resting. In PAH, the average blood pressure is usually greater than 25 mmHg. The disease, which has no cure, causes continuous high blood pressure in the artery that carries blood from the heart to small vessels in the lungs. The muscles within the walls of the arteries may tighten up. This makes the inside of the arteries narrower. The walls of the pulmonary arteries may thicken as the amount of muscle increases in some arteries. Scar tissue may form in the walls of arteries, and as the walls thicken and scar, the arteries become increasingly narrow. Tiny blood clots may form within the smaller arteries, causing blockages. As the vessels narrow, less room is left for blood to flow. The heart can't keep up if the pressure gets too high, and excessively high pressure in the pulmonary artery can cause liquid to leak through the capillary walls and into the lungs. That causes symptoms including fatigue, dizziness, shortness of breath, palpitations or abnormal heartbeat, dry cough, chest pain, swollen ankles or legs, and has frequent fainting spells, eventually heart failure and death. PAH can be inherited, or result from another chronic heart or lung disease.

There are different plausible causes of PAH. It may be due to an already present left-sided heart failure causing pulmonary venous hypertension, then backing up. In such cases it is likely that a left-sided heart failure already was detected, but there are cases where the PAH occurs without any left-sided events. Examples of such reasons include chronic obstructive pulmonary disease (COPD), congenital heart disease, rheumatologic or liver diseases, HIV infection, pulmonary embolism, or any lung disease causing hypoxia (lower levels of oxygen in the blood). Sleep apnea is also a possible reason for PAH. Currently, the disease is often fatal within months of diagnosis.

There are no distinct, common causes to this disease and it is usually not discovered until the right side of the heart has started to fail. This is yet another aspect of why it is considered to be very important to discover the onset of PAH at an early stage.

The treatments for severe PAH include initially medications and additional oxygen, but later on—lung transplant. Transplanting the lung is the most dangerous and least successful of all organ transplants that are performed today. Complications are both common and severe and most patients only live a couple of years.

United States Patent Application Publication No. 2006/0116590 relates to endocardial pressure differential sensing systems and methods for determining a pressure differential between a left heart chamber and a right heart chamber that may be used for detecting different cardiovascular conditions and discriminating between the conditions. The pressure detection is performed by an implantable medical device having leads in different heart chambers and where pressure sensors are provided on the leads. An example of a detectable condition is pulmonary artery hypertension (PAH). PAH is characterized by a rapid increase in the pressure differential, when the sensed pressure in the left chamber remains relatively constant.

United States Patent Application Publication No. 2006/0167359 relates to an implantable medical device with a sensor for sensing hemodynamic pressure over time. The pressure data is processed to form hemodynamic waveform data. A detection of a cardiovascular condition, including PAH, is performed based upon the waveform data. In particular, PAH is detected if the waveform data is of a so-called prominent secondary peak (PSP) type. PSP waveforms include both a prominent primary pressure rise and a prominent secondary pressure rise between diastolic pulmonary pressure and systolic pulmonary pressure values.

Furthermore, the more general scope to detect and monitor pulmonary artery pressure (PAP) naturally includes the specific detection of PAH but in addition also enables early detection of Heart Failure by e.g. indirect monitoring of left ventricular end-diastolic pressure.

SUMMARY OF THE INVENTION

Thus, a need exists for improved capabilities of detection and monitoring of PAP and an object of the present invention is to provide a medical device that includes improved capabilities to monitor and detect pulmonary artery pressure (PAP), that in particular may be realized by techniques presently used in implantable heart stimulators adapted to stimulate the right atrium and right ventricle.

The present invention is based on the insight that the access with two leads to the right side of the heart can potentially offer a way to detect the onset of this disease and distinguish it from other diseases. The basic idea is to acquire two separate measures from the right side of the heart and compare these to each other over time.

Thus, the present invention relates to a medical device, and to a method in a medical device, adapted to monitor pulmonary artery pressure (PAP) of a patient that has a first detector that measures and determines a first parameter ($SV_R$) related to the right ventricular stroke volume of the patient's heart, and a second detector that measures and determines a second parameter ($ER_R$) related to the right ventricular ejection rate of the patient's heart. A pulmonary pressure index ($I_P$) is determined by combining the two parameters, e.g. by determining the ratio of the first and second parameters, wherein variations of the pulmonary pressure index indicates variations of PAP.

According to a preferred embodiment the present invention relates to a medical device specifically adapted to detect and monitor pulmonary artery hypertension (PAH) of a patient.

One way to obtain the above-mentioned parameters is by using intra cardiac impedance, which is the measurement technique used in a preferred embodiment of the present invention, albeit other techniques are possible as well.

According to a preferred embodiment the following parameters are obtained:

1. Right-sided stroke volume ($SV_R$)
2. Right-sided ejection rate ($ER_R$)

The first parameter is the amount of blood that is ejected by the right ventricle in each heart beat. The second parameter is the rate with which the blood is ejected.

If $SV_R$ remains relatively constant and a decrease in $ER_R$ is detected (measured at rest), an increase of pulmonary pressure may be suspected.

That is, as opposed to during exercise where both parameters would increase, due to increased contractility of the heart (positive inotropic effect), or during sleep or decrease of activity where the both would drop as compared to the higher activity level. The important aspect here is to notice if they move in different directions.

The pulmonary pressure index is defined as: $I_P = SV_R/ER_R$ $I_P$ increases with increased pulmonary arterial pressure, and decreases with decreased pulmonary arterial pressure.

DESCRIPTION OF THE PREFERRED EMBODIMENTS

The basic concept includes the acquisition of two parameters which need to capture two special features from the right side of the heart.

The first parameter needs to be proportional to the amount of blood ejected by the right ventricle during each heart beat. It does not have to be an absolute value, but a trend of the same is equally good as we in the end will be monitoring a ratio.

The second parameter needs to capture either the speed with which blood is ejected from the right side of the heart, or, as an alternative, some kind of measure of the current workload of the heart. This may be obtained using a variety of sensors, like a strain gauge, temperature reading or any contractility measure. Herein is primarily described an embodiment where the second parameter being the rate of the ejected blood. Equally applicable is naturally also the ejection time, being the inverse value of the ejection rate.

The determined ratio is proportional to the pulmonary arterial pressure. The reason is that when the pressure increases during the same oxygen demand by the body (that is, no additional stress such as exercise is present), the heart will maintain a constant stroke volume, that is, the amount of blood ejected during each heart beat.

However, to eject the same amount of blood now with the pressure being higher is more difficult. This will manifest itself in that the time it takes to eject the same amount of blood is increased, thus the ejection rate is decreased. As the first parameter remains constant, and the second parameter (in the denominator) decreases, the ratio increases—as does the pulmonary artery pressure.

It is however likely that the parameter referred to as $ER_R$ will not decrease continuously as the pressure increases, but instead in plateaus. This is because the heart will respond to the altered conditions by increased myocardial muscle fiber growth—hypertrophy. This causes the heart to be stronger to overcome the increased pressure, which counteracts the reduced rate for a while until the pressure increases even further.

It should be noted that if the workload-measure is used instead of the ejection rate or the ejection time, this value will change in the opposite direction as the ejection rate, and the algorithms then need to be adjusted accordingly.

As initially stated, there are many ways to obtain each of these parameters. In the following a preferred embodiment will be described using intra-cardiac impedance measurements to obtain the parameters.

Figure 1:
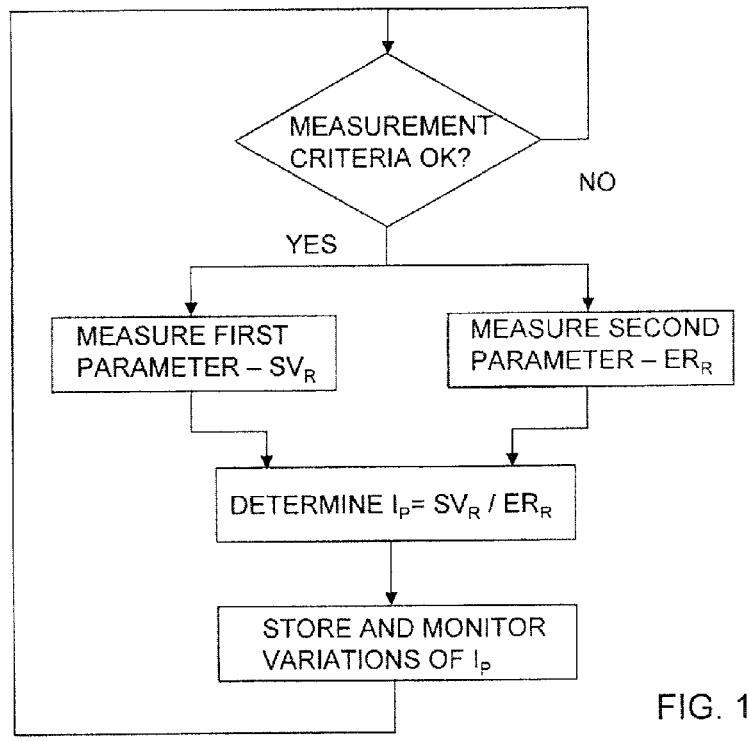
FIG. 1 shows a flow diagram illustrating the present invention.
Figure 2:
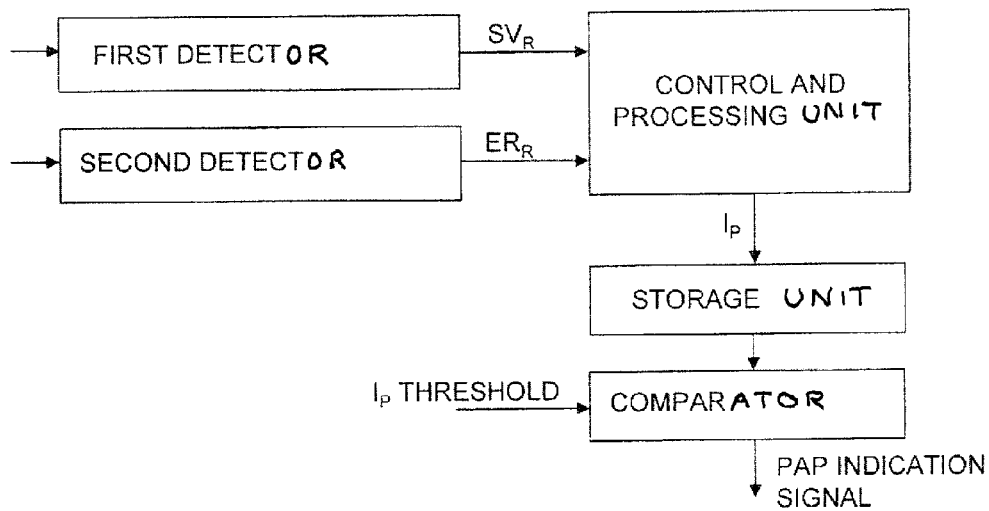
FIG. 2 shows a block diagram illustrating the present invention.

The principle of the invention is illustrated by the flow diagram in FIG. 1, which primarily illustrates the essential steps of the method performed by the medical device, and by the block diagram in FIG. 2. Initially it is checked that the measurement criteria are acceptable, e.g. that the heart rate is within defined limits, that the activity level is within defined values, and that the body posture and the time of the day is acceptable. If the measurement criteria requirement not is fulfilled the criteria are checked at a predetermined later point of time.

If the measurement criteria are acceptable the first and second parameters are measured and the ratio between the parameters is determined. The determined ratio is preferably stored by a storage unit and variations of the stored values may either be performed by a comparator within the medical device by comparing the stored values to one or many IP threshold values. The comparator then generates a PAP indication signal in response of the comparison.

According to a preferred embodiment one or many of the IP thresholds is/are related to pulmonary artery hypertension and the PAP indication signal is then an indication of the degree of PAH.

As an alternative, all or parts of the processing of the measured values are performed by an external device, and the values are then transmitted from the medical device to the external device via conventional telemetry are shown in FIG. 2.

The block diagram of FIG. 2 illustrates the different parts of a preferred embodiment of the present invention. Thus, in FIG. 2 a medical device is illustrated that is adapted to monitor pulmonary artery pressure (PAP) of a patient, and the device has a first detector that measures and determines a first parameter ($SV_R$) related to the right ventricular stroke volume of the patient's heart, and a second detector that measures and determines a second parameter ($ER_R$) related to the right ventricular ejection rate of the patient's heart. A pulmonary pressure index ($I_P$) is determined by combining, in a control and processing unit, the first and second parameters, wherein variations of the pulmonary pressure index indicates variations of PAP. The control and processing unit is connected to the first and second detectors and is adapted to control the timing of the measurements, to perform the calculation of the pulmonary pressure index and to identify variations and trends of consecutively calculated index values. The medical device also includes a storage unit to store the calculated index values and a comparator that compares the calculated $I_P$ value(s) to one or many specified PAP thresholds representing different degrees of PAP, and to generate a PAP indication signal in result of the comparison.

In the specific embodiment of detecting PAH, it is arranged that one or many thresholds relate to different degrees of PAH, and if the pulmonary pressure index increases over time a higher degree of PAH is considered to exist. One of the PAH thresholds may represent a dangerous degree of PAH, and if the $I_P$ value is higher than that threshold an alert function is activated that generates an alarm signal, e.g. a sound signal, to notify the patient.

In the embodiments described herein, the calculated $I_P$-values are evaluated by the medical device, e.g. by the implantable heart stimulator. As an alternative the calculated $I_P$-values may instead be communicated via conventional telemetry to an external programming device, e.g. a programmer, and the comparison and evaluation of the values may then be performed by the external programming device under the supervision of a physician.

The duration of a single measurement procedure to determine the PAP index is a specified time-period, e.g. 10-30 seconds. As an alternative, the duration of the measurement procedure may also be controlled by a specified number of heart cycles, e.g. 10-20 heart cycles, or respiration cycles, e.g. 2-4 respiration cycles, which in either case represents a measurement period of approximately 10-30 seconds.

The measurement procedures are performed at regular intervals, e.g. once every day, or a number of times every day, e.g. 5-10 times every day, and a mean value is then determined for each day.

According to a first embodiment the pulmonary pressure index is determined by the ratio between the first and the second parameter, where the first parameter is related to the stroke volume of the right ventricle, and the second parameter is related to the ejection rate of the right ventricle.

Preferably, the first detector is an impedance measurement device adapted to measure the intra cardiac impedance of the right ventricle, and that the first parameter is determined in dependence on the measured impedance. Naturally, alternative measurement methods of determining the right ventricular stroke volume may be used, e.g. by using an intracardiac pressure sensor (see e.g. U.S. Pat. No. 7,024,244).

According to a second embodiment the first and second detector are impedance measurement devices adapted to measure the intra cardiac impedance of the right ventricle, and that the first and second parameters are determined in dependence of the measured impedance. It will be further discussed in the following, in relation to FIG. 5, how the ejection rate is determined from an impedance signal.

As indicated above the second parameter may alternatively instead be related to the current workload ($W_R$) of the heart. In that case the pulmonary pressure index is determined by the product of the first and the second parameter:

$$I_P = SV_R \times W_R$$

The workload may be measured by e.g. a strain gauge, a temperature sensor or a contractility sensor.

According to a preferred embodiment the device is an implantable medical device, and in particular an implantable heart stimulator, e.g. a pacemaker, a cardioverter or a defibrillator.

Figure 3:
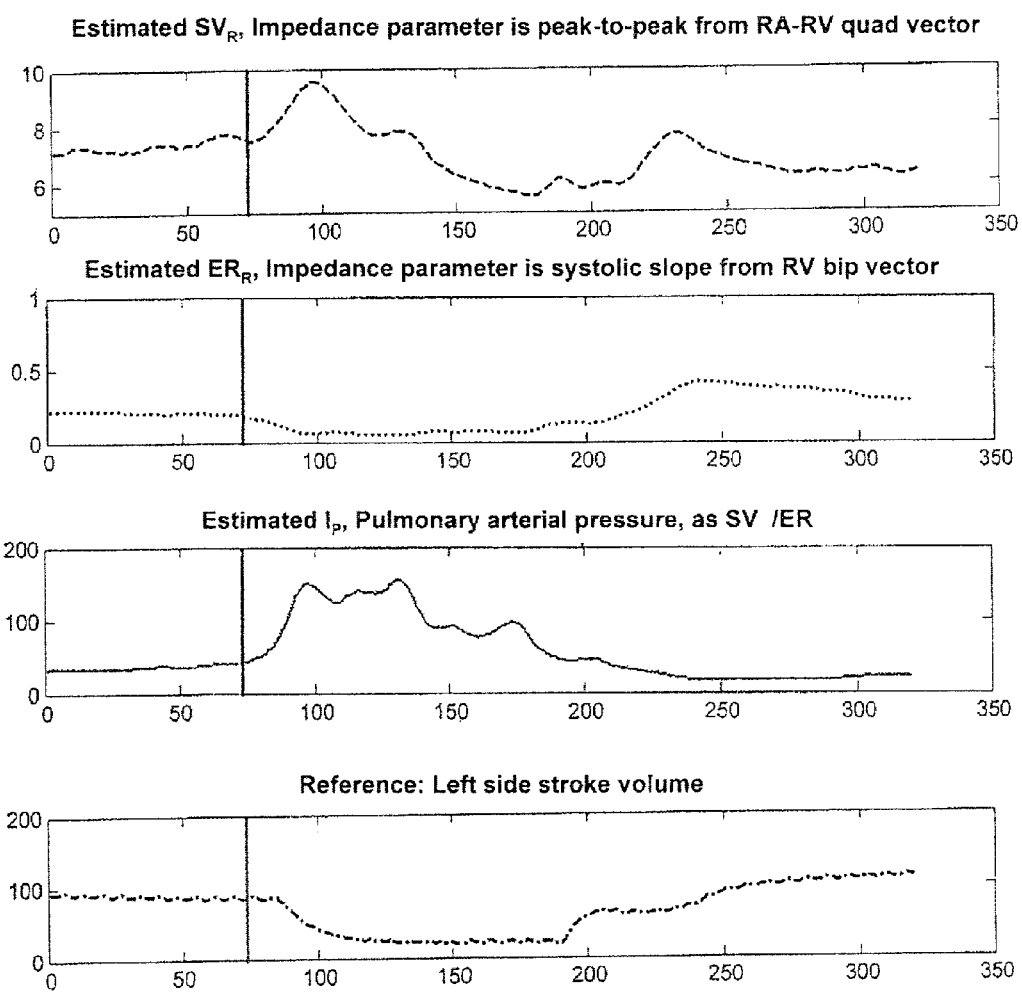
FIG. 3 shows four graphs illustrating various aspects of the present invention.

FIG. 3 discloses four graphs illustrating different parameters of the present invention. The X-axis denotes time in seconds, and the Y-axis denotes impedance (first and second graphs), the value of $I_P$ (third graph) and volume in ml (fourth graph).

The first graph, from above, shows the estimated stroke volume as being the peak-to-peak impedance value measured by a quadruple impedance technique between the right atrial (RA) and the right ventricle (RV) leads. The peak to peak value is easily obtained and is simply the difference between the maximum and the minimum impedance value during a heart cycle. Several other options are naturally possible. There is a good correlation between the peak-to-peak value of the transvalvular intra-cardiac impedance from the right side and the stroke volume/cardiac output. This correlation is clearly shown in FIG. 3 when comparing the upper graph with the lowest graph that shows a reference left side stroke volume signal. The x-axes in the graphs denote consecutive heart cycles and the graphs show one value per heart cycle.

The second graph shows the estimated ejection rate as being the systolic slope of an RV bipolar vector of an impedance value. The ejection rate parameter is easily obtained by calculating the systolic slope of a cardiogenic impedance signal. Several vectors are possible when acquiring the impedance signal. Two of these are the previously discussed transvalvular configuration, and another waveform is obtained from a bipolar recording between the RV ring and the RV tip.

Figure 5:
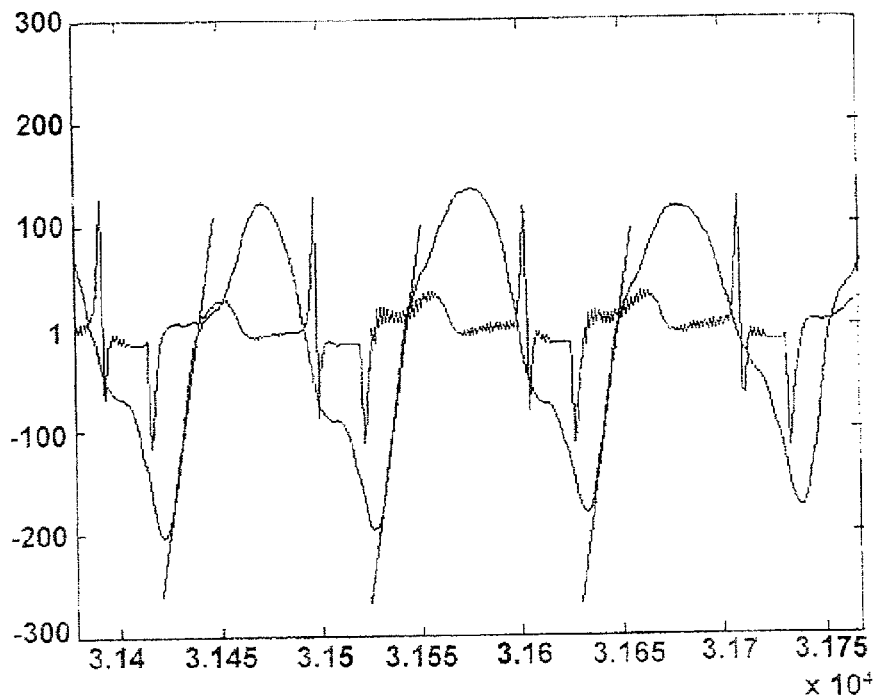
FIG. 5 shows a graph illustrating how the ejection rate may be determined according to one embodiment of the present invention.

FIG. 5 shows an example of how the systolic slope may be defined. In FIG. 5 an atrial IEGM and the transvalvular impedance are shown during three full heart cycles and the straight lines indicates how the systolic slopes are defined.

The derivative of the line represents the rate with which blood is ejected from the chamber, i.e. the $ER_R$-parameter.

The third graph of FIG. 3 shows the calculated $I_P$ which estimates the pulmonary arterial pressure.

And finally, the fourth graph shows a reference signal is of the left sided stroke volume (black, dash-dot) as recorded with a transonic flux probe around the base of the aorta.

As the pulmonary arterial pressure rises, less blood will flow to the left side (as can be seen also in the slowly decreasing right sided stroke volume). This is why we see a drop in the left sided stroke volume some ~10 heart beats after the occlusion.

In FIG. 3, the black, vertical lines denote the onset of the occlusion. It is also interesting to see that the initial slight pressure increase (before the balloon catheter is fully expanded) provokes a slight stress reaction with increased stroke volume on the right side which gradually decreases. The estimate of the pulmonary arterial pressure, $I_P$ (third graph), clearly shows the increase in pressure during the occlusion.

Figure 4:
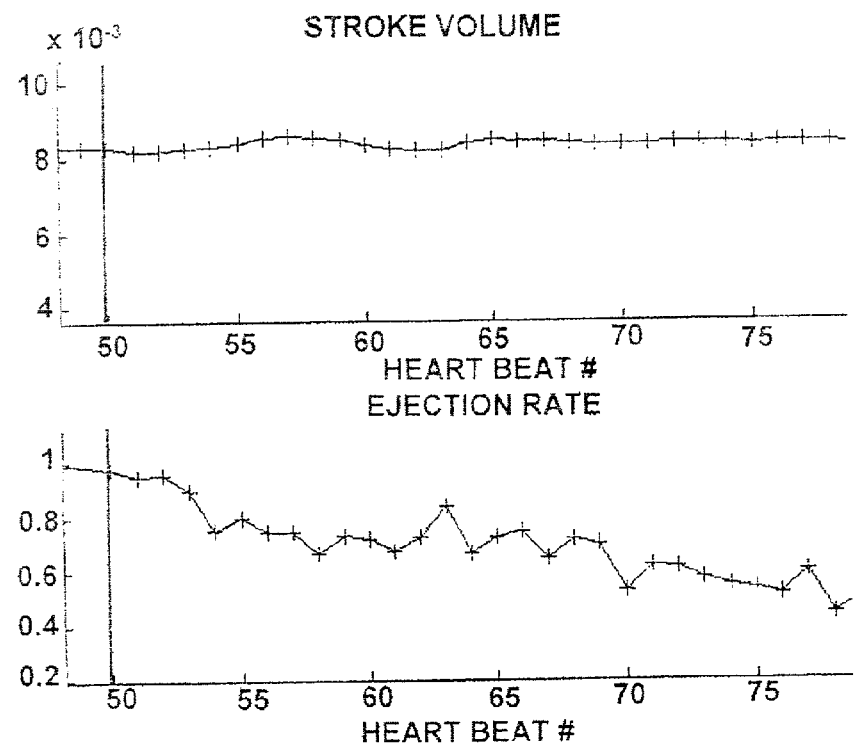
FIG. 4 shows two graphs illustrating the detected stroke volume and ejection rate, respectively.

Pulmonary artery occlusion was performed on canines at a pre-clinical test. A result from such a measurement is shown in FIG. 4. This is prior to heavy occlusion, after which the stroke volume also drops. However, at an earlier stage the introduction of the catheter increases the pulmonary arterial pressure due to the fact that it takes up space and starts to inflate, this is indicated by the black vertical line. We clearly see a drop in the $ER_R$-parameter, whereas the $SV_R$-parameter remains stable. This suggests that it is indeed possible to trend changes in pulmonary arterial pressure, and that one way to do that is by means of using intra-cardiac impedance measurements.

The present invention is not limited to the above-described preferred embodiments. Various alternatives, modifications and equivalents may be used. Therefore, the above embodiments should not be taken as limiting the scope of the invention, which is defined by the appending claims.

Although modifications and changes may be suggested by those skilled in the art, it is the intention of the inventor to embody within the patent warranted heron all changes and modifications as reasonably and properly come within the scope of his contribution to the art.

I claim:

1. A medical device to monitor pulmonary artery pressure (PAP) of a patient, comprising:
   a first detector configured to measure and determine a first parameter ($SV_R$) indicative of a right ventricular stroke volume of the patient's heart;
   a second detector configured to measure and determine a second parameter ($ER_R$) indicative of speed of blood ejected from a right ventricle of the patient's heart; and
   a processing unit configured to determine a pulmonary pressure index ($I_P$) by combining the first and second parameters, with variations of the pulmonary pressure index indicating variations of PAP.

2. Medical device according to claim 1, wherein said processing unit is configured to use the determined pulmonary pressure index ($I_P$) to detect pulmonary artery hypertension (PAH).

3. Medical device according to claim 1, wherein said processing unit is configured to use the determined pulmonary pressure index ($I_P$) to monitor left ventricular end diastolic pressure.

4. Medical device according to claim 1, wherein said processing unit is configured to determine the pulmonary pressure index as a ratio between the first parameter and the second parameter.

5. Medical device according to claim 1, further comprising a control unit that controls said first and second detectors to respectively measure said first and second parameters during a predetermined time-period.

6. Medical device according to claim 5 wherein the control unit controls said first and second detectors to respectively measure said first and second parameters as consecutive measurements performed at regular intervals.

7. Medical device according to claim 1, further comprising a control unit that controls said first and second detectors to respectively measure said first and second parameters during a predetermined number of heart cycles.

8. A medical device as claimed in claim 7 wherein the control unit controls said first and second detectors to respectively measure said first and second parameters as consecutive measurements performed at regular intervals.

9. Medical device according to claim 1, further comprising a storage unit, in communication with the output of the processing unit, that stores values that are determined for the pulmonary pressure index during a number of heart cycles.

10. Medical device according to claim 1, further comprising a comparator that compares a calculated $I_P$ to one or many specified PAP thresholds representing different levels of PAP, and generates a PAP indication signal in result of said comparison.

11. Medical device according to claim 10, wherein the comparator employs, as said one or many specified PAP thresholds, a threshold that represents a dangerous level of PAP, and when the $I_P$ value is higher than the PAP threshold an alert function is activated that generates an alarm signal to notify the patient.

12. Medical device according to claim 10, wherein at least one of the specified PAP thresholds represents pulmonary artery hypertension (PAH).

13. Medical device according to claim 12, wherein said processing unit is configured to determine if the pulmonary pressure index increases over time and, if so, to emit a signal indicating a higher degree of PAH exists.

14. Medical device according to claim 1, wherein the first detector is an impedance measurement means measures intra cardiac impedance of the right ventricle, and the first parameter is determined in dependence of the measured impedance.

15. Medical device according to claim 1, wherein the first and second detectors are impedance measurement means that measure intra cardiac impedance of the right ventricle, and the first and second parameters are determined in dependence of the measured impedance.

16. Medical device according to claim 1, wherein said first and second detectors and said processing unit are configured to be implantable.

17. Medical device according to claim 1, further comprising a telemetry unit connected to said output of said processing unit that communicates determined $I_P$-values via telemetry to an external programming device.

18. A medical device as claimed in claim 1 further comprising a pulse generator and at least one electrode lead configured to generate and deliver stimulation pulses in vivo to the patient's heart, and a pacing control unit connected to said output of said processing unit and configured to control generation of said stimulation pulses dependent on said pulmonary pressure index.

19. Method in a medical device adapted to monitor pulmonary artery pressure (PAP) of a patient, the method comprises the steps of:
   a) measuring and determining, by a first detector, a first parameter ($SV_R$) indicative of the right ventricular stroke volume of the patient's heart;

b) measuring and determining, by a second detector, a second parameter ($ER_R$) indicative of speed of blood ejected from a right ventricle of the patient's heart; and c) in a processor, combining the first and second parameters to determine a pulmonary pressure index ($I_P$), with variations of the pulmonary pressure index indicating variations of PAP.

20. Method according to claim 19, further comprising using said pulmonary pressure index to detect and monitor pulmonary artery hypertension (PAH).

21. Method according to claim 19, further comprising using the determined pulmonary pressure index ($I_P$) to monitor left ventricular end diastolic pressure.

22. Method according to claim 19, further comprising determining the pulmonary pressure index has the ratio between the first and the second parameter.

23. Method according to claim 19, further comprising measuring said first and second parameters during a predetermined time-period.

24. Method according to claim 19, further comprising measuring said first and second parameters during a predetermined number of heart cycles.

25. Method according to claim 19, further comprising measuring intra cardiac impedance of the right ventricle, and determining the first and second parameters dependent on the measured impedance.

26. A medical device to monitor pulmonary artery pressure (PAP) of a patient, comprising:
   a first detector configured to measure and determine a first parameter ($SV_R$) indicative of the right ventricular stroke volume of the patient's heart;
   a second detector configured to measure and determine a second parameter ($W_R$) indicative of the workload of the patient's heart; and
   a processing unit configured to determine a pulmonary pressure index ($I_P$) by combining the first and second parameters, with variations of the pulmonary pressure index indicating variations of PAP.

27. Medical device according to claim 26, wherein said processing unit is configured to determine the pulmonary pressure index as the product of the first and the second parameter.

28. Medical device according to claim 26, wherein the second detector is selected from the group consisting of a strain gauge, a temperature sensor or a contractility sensor.

29. Method in a medical device adapted to monitor pulmonary artery pressure (PAP) of a patient, the method comprises the steps of:
   a) measuring and determining, by a first detector a first parameter ($SV_R$) indicative of the right ventricular stroke volume of the patient's heart;
   b) measuring and determining, by a second, detector, a second parameter ($W_R$) indicative of the workload of the patient's heart; and
   c) in a processor, combining the first and second parameters to determine a pulmonary pressure index ($I_P$), with variations of the pulmonary pressure index indicating variations of PAP.

* * * * *